US006602505B2

(12) United States Patent
Douvas et al.

(10) Patent No.: US 6,602,505 B2
(45) Date of Patent: Aug. 5, 2003

(54) VIRAL CHIMERAS COMPRISED OF CAEV AND HIV-1 GENETIC ELEMENTS

(75) Inventors: Angeline Douvas, Pasadena, CA (US); Tyler B. Parr, Chula Vista, CA (US)

(73) Assignee: University of Southern California, Los Angeles, CA (US)

( * ) Notice: Subject to any disclaimer, the term of this patent is extended or adjusted under 35 U.S.C. 154(b) by 292 days.

(21) Appl. No.: 09/302,171

(22) Filed: Apr. 29, 1999

(65) Prior Publication Data

US 2001/0039669 A1 Nov. 8, 2001

Related U.S. Application Data
(60) Provisional application No. 60/083,652, filed on Apr. 30, 1998.

(51) Int. Cl.[7] .................. A61K 39/21; C07H 21/02; C12N 7/01
(52) U.S. Cl. .................. 424/199.1; 424/187.1; 424/188.1; 424/202.1; 424/207.1; 424/208.1; 435/5; 435/7.1; 435/235.1; 435/236; 435/320.1; 514/44; 530/350; 536/23.72
(58) Field of Search .................. 424/187.1, 188.1, 424/199.1, 202.1, 207.1, 208.1; 435/5, 7.1, 235.1, 320.1, 236; 514/44; 530/350; 536/23.72

(56) References Cited

U.S. PATENT DOCUMENTS

| 5,142,025 A | 8/1992 | Putneye t al. |
| 5,561,064 A | 10/1996 | Marquet et al. |
| 5,580,859 A | 12/1996 | Felgner et al. |
| 5,589,466 A | 12/1996 | Felgner et al. |
| 5,703,055 A | 12/1997 | Felgner et al. |
| 5,714,374 A | 2/1998 | Arnold et al. |
| 5,716,826 A | 2/1998 | Gruber et al. |
| 5,770,357 A | 6/1998 | Douvas et al. |
| 5,770,428 A | 6/1998 | Boris-Lawrie |
| 5,851,813 A | 12/1998 | Desrosiers |
| 5,879,925 A | 3/1999 | Rovinski et al. |
| 5,885,578 A | 3/1999 | Salk et al. |
| 5,889,176 A | 3/1999 | Rovinski et al. |
| 5,994,516 A | 11/1999 | Pancino et al. |

FOREIGN PATENT DOCUMENTS

| WO | WO9600784 | 1/1996 |
| WO | WO9630527 | 10/1996 |
| WO | WO9733615 | 9/1997 |

OTHER PUBLICATIONS

Luciw et al. PNAS, USA. vol. 92, pp. 7490–7494, Aug. 1995.*
Knowles et al. J. Virol. vol. 65, No. 11 pp. 5744–5750, Nov. 1991.*
Abergel C, et al., Virol 1999 Jan.; 73(1):751–3 " "Hidden-"dUTPase sequence in human immunodeficiency virus type 1 gp120".

Abimiku, et al., Nat. Med. 1:321–329 (1995

OTHER PUBLICATIONS

Chiu IM, et al., Nature 1985 Sep. 26–Oct. 2; 317(6035):366–8 "Nucleotide sequence evidence for relationship of AIDS retrovrus to lentiviruses".

Cohen, Science, vol. 262, 980–981, Nov. 1993, "Jitters jeopardize AIDS vaccine trials".

Cooney, et al., Proc. Natl. Acad. Sci. 90:1882–1886 (1993), "Enhanced immunity to human immunodeficiency virus (HIV) envelope elicited by a combined vaccine regiment consisting of priming with a vaccinia recominant expressing HIV envelope and boosting with gp160 protein".

Cooney, et al., 337:567–572 (1991), "Safety of and immunological response to a recombinant vaccinia virus vaccine expressing HIV envelope glycoprotein".

Crawford, et al., Science 207, 997–999 (1980), "Chronic arthritis in goats caused by a retrovirus".

Crow, et al., Cell. Immunol. 121:99–112 (1989), "Human Peripheral Blood T Helper Cell–Induced B Cell Activtion Results in B Cell Surface Expression of the CD23 (BLAST–2) Antigen".

Cummins, et al., Blood, vol. 77, No. 5, Mar. 1, 1991, 1111–1117, "Preparation and Characterization of an Intravenous Solution of IgG From Human Immunodeficiency Virus–Seropositive Donors".

Douvas, et al., Aids Research and Human Retroviruses, vol. 10, No. 3, 253–262 (1994), "Cross–Reactivity Between Autoimmune Anti–U1 snRNP Antibodies and Neuralizing Epitopes of HIV–1 gp120/41".

Douvas, Proc. Natl. Acad. Sci. USA, vol. 79, 5401–5405 (1982), "Autoantibodies Occurring in Two Different Rheumatic Diseases React with the Same Nuclear Ribonucleoprotein Particle".

Eichberg, et al., J. Virol. 62:3804–3808 (1987), "T–cell responses to human immunodeficiency virus (HIV) and its recombinant antigens in HIV–infected chimpanzees".

Exceler, et al., AIDS 11:S127–S137 (1997), "The prime–boost concept applied to HIV preventive vaccines".

Ferrari, et al., Proc. Natl. Acad. Sci. 94:1396–1401 (1997), "Clade B–based HIV–1 vaccines elicit cross–clade cytotoxic T lymphocyte reactivities in unifected vlunteers".

Fields, et al., Virology Third Ed: Lippincott–Raven Publishers (1996) p. 21.

Gallimore, et al., Nat. Med. 1:1167–1173 (1995), "Early suppoeression of SIV replication by CD8+ nef–specific cytotoxic T cells in vaccinated macaques".

Garry, et al., Retroviridae 4:491–603 (1995), "Retroviruses and Their Roles in Chronic Inflammatory diseases and Autoimmunity".

Gonda, et al., Retroviridae 3:83–109 (1994), "The Lentiviruses of Cattle".

Gonda, et al,., Proc. Natl. Acad. Sci., USA 83:4007–4111 (1986), "Human T–cell lymphotropic virus type III shares sequence homology with a family of pathogenic lentiviruses".

Hasse, A.T. Nature 322–130–136 (1986), "Pathogenesis of lentivirus infections".

Haga T, et al., Microbiol Immunol 1998; 42(4):245–51 "A new approach to AIDS research and prevention: the use of gene–mutated HIV–1/SIV chimeric viruses for anti–HIV–1 live–attenuated vaccines".

Harmache, et al., J. Virol. 69:3247–3257 (1995), "The vif Gene Is Essential for Efficient Replication of Caprine Arthritis Encephalitis Virus in Goat Synovial Membrane Cells and Affects the Late Steps of the Virus Replication Cycle".

Harmache A, et al., J Virol Sep. 1995; 69(9):5445–5454 "The Caprint Arthritis Encephalitis Virus tat Gene is Dispensable for Efficient Viral Replication In Vitro and In Vivo."

Haynes, Science, vol. 260, 1279–1286, May 1993, "Scientific and Social Issues of Human Immunodeficiency Virus Vaccine Development".

Heilman, et al., Nature Medicine Vaccine Supplement, vol. 4, No. 5, May 1998, 532–534, "HIV vaccines—where are we going?".

Hess JL, et al., J Virol Nov. 1986; 60(2):385–93, "Nucleotide sequence and transcriptional activity of the caprine arthritis–encephalitis virus long terminal repeat".

Hullinger GA, et al., Virology Jan 1993; 192(1):328–31, "Caprine arthritis–encephalitis lentivirus SU is the ligand for infection of caprine synovial membrane cells."

Jackson MK, et al., Virology Jan 1991;180(1):389–94, "Genetic structure of the pol–env region of the casprine arthritis–encephalitis lentivirus genome".

Johnson, et al., Proc. Natl. Acad. Sci. USA, vol. 89, 2175–2179, Mar. 1992, "Inactiviated Whole–virus vaccine derived from a proviral DNA clone of simian immunodeficiency virus induces high levels of neutralizing antibodies and confers protection against heterologous challenge".

Knowles, et al., J. Virol. Nov. 1991; 65(11):5744–50, "Structure and genetic variability of envelope glycoproteins of two antigenic variants of caprine arthritis–encephalitis lentivurus".

Knowles, et al., J. Virol. 64:2396–2398 (1990), "Severity of Arthritis Is Predicted by Antibody Responses to gp135 in Chronic Infection with Caprine Arthritis–Encephalitis Virus".

Lambert JS, Pediatric AIDS and HIV Infection: Fetus to Adolescent, vol. 6, No. 5, 1995, 300–302, "The Prevention of Maternal–Fetal HIV–1 Infection throught Passive Antibody Products (HIVIG) and Active Immunization (AIDS Vaccines)".

Li, et al., J. AIDS 5:639–646 (1992), "Infection of cynomolgus monkeys with a chimeric HIV–1/$SIV_{mac}$ virus that expresses the HIV–1 envelope glycoproteins".

Luciw, et al., Proc. Natl. Acad. Sci. 92:7490–7494 (1995), "Persistent infection of rhesus macaques with T–celo–line–tropic and macrphage–tropic clones of simian/human immunodeficiency viruses (SHIV)".

McElrath, et al., J. Infect. Dis. 169:41–47 (1994), "Immune responses elicited by recombinant vaccinia–human immunodeficiency virus (HIV) envelope and HIV envelope protein: analysis of the durability of resonses and effect of repeated boosting".

Michaels FH, et al., Rheum Dis Clin North Am Feb. 1991; 17(1):5–23, "Lessons from caprine and ovine retrovirus infections".

Perry, et al., J. Infect. Dis. 171:328–334 (1995), "Depressed CD4+ Lymphocyte Proliferative Response and Enhanced Antibody Response to Viral Antigen in Chronic Lentivirus–Induced Arthritis".

Prince, et al., AIDS Research and Human Retroviruses, vol. 7, No. 12, 971–973, 1991, "Prevention of HIV Infection by Passive Immunization with HIV Immunoglobulin".

Pyper JM, Clements JE, Gonda MA, Narayan O, J Virol May 1986; 58(2):665–70, "Sequence Homology between Cloned Caprine Arthritis Encephalitis Virus and Visna Virus, Two Neurotropic Lentiviruses".

Quesada–Rolander, et al., AIDS Research and Human Retroviruses, vol. 12, No. 11, 993–999, 1996 "Protection against Mucosal SIV$^{SM}$ Challenge in Macaques Infected with a Chimeric SIV that Expresses HIV Type 1 Envelope".

Raz, et al., Proc. Nat. Acad. Sci. 91:9519–1923 (1994), "Intradermal gene immunization: The possible role of DNA uptake in the induction of cellular immunity to viruses".

Saltarelli, et al., Virology 197(1):35–44 (1993), "The CAEV that Gene Trans–activates the Viral LTR and Is Necesary for Efficient Viral Replication".

Saltarelli, et al., Virology 179:347–364 (1990), "Nucleotide Sequence and Transcriptional Analysis of Molecular Clones of CAEV Which Generate Infectious Virus".

Schoborg RV, et al., Virology Jul. 1994; 202(1):1–15, "A Rev Protein Is Expresin in Caprine Arthritis Cncephalitis Virus (CAEV)–Infected Cells and Is Required for Efficient Viral Replication."

Serruya, et al, AIDS Res. and Hum. Retrovir.: vol. 10 S. 1L PS54 (1994), "Identification of novel CAEV–like lentivirus pol sequences and CAEV–antigen reactivity in HIV–associated Kaposi's sacrcoma lesion".

Shen, et al., Science 252: 440–443 (1991), "Recombinant virus vaccine–induced SIV–specific CD8+ cytotoxic T lymphocytes".

Shibata, et al., J. Virol 71:8141–8148 (197), "Live, Attenuated Simian Immunodeficiency Virus Vaccines Elicite Potent Resistance Against a Challenge with a Human Immunodeficiency Virus Type 1 Chimeric Virus".

Shibata, et al., J. Virol 65(7):3514–3520 (1991), "Generation of a Chimeric Human and Simian Immunodeficiency Virus Infectious to Monkey Peripheral Blood Mononuclear Cells".

Shibata, et al, J. Virology 64:5861–5868 (1990), "Generation and Characterization of Infectious Chimeric Clones Between Human Immunodeficiency Virus Type 1 and Simian Immunodeficiency Virus from an African Green Monkey".

Taylor, et al., Vaccine 6:497–503 (1988), "Recombinant fowlpox virus induces protective immunity in non–avian species".

Wain–Hobson, et al., Virology 209, 297–303 (1995), "Erratic G→ A hypermutation within a complete caprine arthritis–encephalitis virus (CAEV) provirus".

Wills, et al., J. Virol. 65(7):3804–3812 (1991), "Suppression of Retroviral MA Delections by the Amino–Terminal Membrane–Binding Domain of p60$^{src}$".

Yaniv A, et al., Virology Sep. 1985; 145(2):340–5, "Molecular cloning of integrated caprine arthritis–encephalitis virus".

York–Higgins, et al., Journal of Virology, Aug. 1990; 64(8):4016–4020, "Human Immunodeficiency Virus Type 1 Cellular Host Range, Replication, and Cytopathicity Are Linked to the Envelope Region of the Viral Genome".

Database Aidsline on Dialog, No. 97927046, Douvas, et al., abstract, Conf. Adv. AIDS Vaccine Dev. Amy 4–7, 1997, "Human–infecting forms of caprine arthritis–encephalitis virus (CAEV) in HiV vaccine strategies".

Database Medline on Dialog, US National Library of Medicine, (Bethesda, MD, USA), No. 97354064, Ding, et al., abstract, Viral Immunology, vol. 10, No. 2, pp. 111–115 (1997), "Immune responses in goats to caprine arthritis–encephalitis virus".

Database Medline on Dialog, US National Library of Medicine (Bethesda, MD, USA), No. 89213286, Straub, O.C., abstract, Intervirology, vol. 30, Supp. 1, pp. 45–50, (1989), "Caprine arthritis encephalitis—a model for AIDS?".

Webster's II New Riverside University Dictionary, pp. 626 and 1200 (1994).

International Search Report, International Application No. PCT/US99/06556, Sep. 17, 1999.

* cited by examiner

VIRAL CHIMERAS COMPRISED OF CAEV AND HIV-1 GENETIC ELEMENTS

This application claims the benefit of U.S. Provisional Application No. 60/083,652, filed Apr. 30, 1998.

This invention was made with government support under Contract No. 5-U01-HP-32632 awarded by the National Institutes of Health. The government has certain rights in the invention.

BACKGROUND OF THE INVENTION

Field of the Invention

This invention relates generally to the fields of immunology and medicine and more specifically to methods for generating an immune response against HIV-1.

Background Information

The incidence of acquired immunodeficiency syndrome (AIDS) has reached epidemic proportions, particularly in third world countries in Africa, Asia and the Caribbean. The causative agent of AIDS is the human immunodeficiency virus (HIV-1). HIV-1 is a primate lentivirus believed to have crossed species to humans from a monkey population in Africa in the 1950's.

In humans, HIV-1 infects two primary cell types: macrophages and T lymphocytes. In a typical transmission event, a macrophage-tropic strain is passed from a bodily fluid of one person to macrophages in the skin or mucosa of another. Initially, the virus can replicate in macrophages without producing clinical disease. As the infection progresses, divergent strains are produced as a result of the virus's rapid mutation rate, due at least in part to a reverse transcriptase having poor fidelity. Eventually, T cell-tropic strains arise which result in depletion of the immune system and the clinical manifestations known as AIDS.

This progression typically takes from six to ten years or more, depending, in part, on host immune system factors. However, a T-cell-tropic HIV-1 strain can also be transmitted directly leading to a much more rapid course of infection. As the disease progresses, the host's immune system is unable to replace the T cell population as quickly as it is depleted by viral infection, leading to catastrophic decreases in T cell levels. As a result, AIDS patients typically die from infections that normally would cause, at worst, a mild illness in a healthy individual.

Despite the expenditure of billions of dollars for research, only moderate progress has been made in treating the disease. Initially, therapy was limited to methods of treating the opportunistic infections which arose in the immunocompromised patients. Later, nucleoside analogs such as AZT, ddC and ddI were identified that could interfere with HIV-1 replication. These drugs, particularly in combination, prolonged the lives of some AIDS patients. More recently, a class of drugs called protease inhibitors has proven to be even more effective in inhibiting HIV-1 replication. When used in combination with nucleoside analogs, protease inhibitors have reduced viral titers in some patients to undetectable levels. Recently, the death rate from AIDS in the United States has decreased for the first time since the start of the epidemic. This is believed to be a result of such treatment regimens, at least in part, along with educational programs discouraging high risk behaviors.

Hopes for these treatment regimens have been curtailed by the subsequent emergence of resistance to multidrug cocktails. Additionally, while circulating levels of virus drops in some patients treated with combinations of protease inhibitors and nucleoside analogs, such treatment does not result in elimination of the virus from those patients. Viral reservoirs are believed to remain even in patients having no detectable circulating virus, for example in the lymphatic system and in macrophages. Furthermore, even where no circulating virus is present, viral spread may still occur as a result of the fusogenic properties of cells already infected with HIV-1. Finally, the drug cocktails have not produced positive results in all patients, and therefore appear unlikely to be effective against all viral strains.

The cumbersome dosing regimen required by multidrug therapies also creates problems with patient compliance. As treated patients survive for longer periods of time, these compliance issues will only increase, leading to the possibility that such patients may eventually present avenues for the generation and spread of HIV-1 strains resistant to the drug cocktails.

Furthermore, although some patients in the U.S. can afford such expensive combination therapies, the cost of such drugs far exceeds the annual income of many third world individuals. This is particularly alarming because of the rapid increase in HIV-1 transmission in the third world.

Clearly, a preferable approach would be to prevent HIV-1 transmission. Vaccines are a logical choice to accomplish this. For example, vaccines have been used to prevent or reduce the severity of various viral diseases, including polio, measles, smallpox and influenza. In addition, a vaccine can stimulate the immune system in individuals already infected with a virus. For example, rabies vaccine is only administered after a transmission event, such as a bite from an infected animal.

Numerous attempts have been made to develop a vaccine that would increase a person's resistance to HIV-1 infection, but the approaches to date suffer from serious limitations. For example, vaccines composed of portions of an HIV-1 protein or using a killed HIV-1 virus have been produced. However, HIV-1 mutates rapidly during viral replication, producing new variants faster than the immune system can react. As a result, an immune response which is stimulated against a particular HIV-1 protein or strain can be ineffective against variants that arise during infection. Furthermore, vaccination with portions of HIV-1 surface proteins can stimulate the production of antibodies that may facilitate, rather than prevent, HIV-1 infection. Attenuated vaccines, which consist of live but reproductively defective viruses, also have been proposed. However, there is justified concern for injecting such an HIV-1 virus into an individual, particularly an otherwise healthy person. Thus, a need exists for a vaccine that provides an immune response against HIV-1 but does not carry the attendant risks and limitations associated with the use of HIV-1 as the vaccinating agent.

One approach to developing an animal model to study HIV-1 infection and possible vaccine strategies has been the generation of a recombinant virus between simian immunodeficiency virus (SIV) and HIV-1, or SHIV, which can infect lower primates. The in vivo behavior of the SHIV model has elucidated many aspects of retroviral pathology and host response. These include the demonstration that host range, cytopathicity and the specificity of neutralizing antibodies are determined by the envelope sequences (Luciw et al., Proc. Natl. Acad. Sci. 92:7490-7494 (1995)). Used as live-attenuated vaccines, SHIVs have been shown to effectively protect macaques against mucosal challenge with SIV (Baba et al., Science 267:1820-1825 (1995); Quesada-Rolander et al., AIDS Res. Hum. Retro. 12:993-999 (1996)).

In 1985 and 1986, the relationship between the nucleotide and amino acid sequences of HIV-1 and caprine arthritis-encephalitis virus (CAEV) was described. CAEV and HIV-1 are closely related phylogenetically and share a high degree of homology, including, for example, between their RNA-dependent DNA polymerases (pol) and between gp120/41 in HIV-1 and gp135/38 in CAEV (see, for example, Gonda et al., Proc. Natl. Acad. Sci., USA 83:4007-4111 (1986); Gonda et al., Retroviridae 3:83-109 (1994); Garry et al., Retroviridae 4:491-603 (1995)).

CAEV infects goats and causes abnormalities of the immune system in some infected animals (see, for example, Banks et al., Arthrit. Rheum. 30:1046-1053 (1987); Crawford et al., Science 207:997-999 (1980)). CAEV is associated with three disease syndromes in goats: arthritis, which occurs in 20-30% of infected animals; leukoencephalitis, which occurs in young animals; and sporadic neurologic disease, which occurs in adult goats. However, 60% of infected animals are long-term non-progressors, developing no clinically apparent lesions (Cheevers et al., Lab. Invest. 58:510-517 (1988); Knowles et al., J. Virol. 64:2396- 2398 (1990); Perry et al., J. Infect. Dis. 171:328-334 (1995)). CAEV infection is found worldwide, with an estimated 80% of goat herds suffering from some level of infection.

CAEV is transmitted among goats through infected milk, particularly colostrum, and infection is spread by the agricultural practice of pooling colostrum to feed young animals. CAEV multiplies in cells of the monocyte/macrophage lineage and in fibroblast cell lines, but does not infect T cells. Macrophages expressing CAEV are distributed in the synovia, lungs, central nervous system, lymph nodes, spleen, gastro-intestinal tract and mammary glands of infected goats.

There is a need in the art for a non-pathogenic lentivirus which can generate an immune response against HIV-1 in a primate, particularly a human.

SUMMARY OF THE INVENTION

The present invention satisfies this need and provides additional advantages. In one embodiment, a polynucleotide comprising a chimeric retroviral genome is provided comprising elements of CAEV and HIV-1. This chimeric retrovirus is referred to as a CHIV. The retroviral genome includes the regulatory sequences from CAEV along with such other CAEV coding sequences as are required to render the CHIV nonpathogenic, as well as an HIV-1 env gene. Other retroviral genes can be provided from either CAEV or HIV-1. The CHIV must be able to propagate in at least one mammalian host cell.

The invention further provides a CHIV immunogen capable of stimulating an immune response. In one embodiment, the CHIV immunogen is a viral particle capable of infecting a host cell. In another embodiment, the CHIV immunogen is a polynucleotide expression construct which can be expressed when introduced into an organism in order to stimulate an immune response to the expression products.

The present invention also provides a vaccine comprising a CHIV immunogen and a pharmaceutically acceptable carrier. A vaccine of the invention is useful, for example, to stimulate an immune response against human immunodeficiency virus (HIV-1) in a human or other primate.

The invention also provides a method of stimulating an immune response in an individual against HIV-1 by administering a CHIV immunogen to the individual. Such a method is useful, for example, to increase the resistance to HIV-1 infection of an individual not previously exposed to HIV-1, or to reduce the severity of a pathology caused by HIV-1 in an HIV-1 infected individual. In addition, the invention provides a method of stimulating an immune response in vitro by contacting a lymphocyte with a CHIV immunogen.

DETAILED DESCRIPTION OF THE INVENTION

Figure 1:
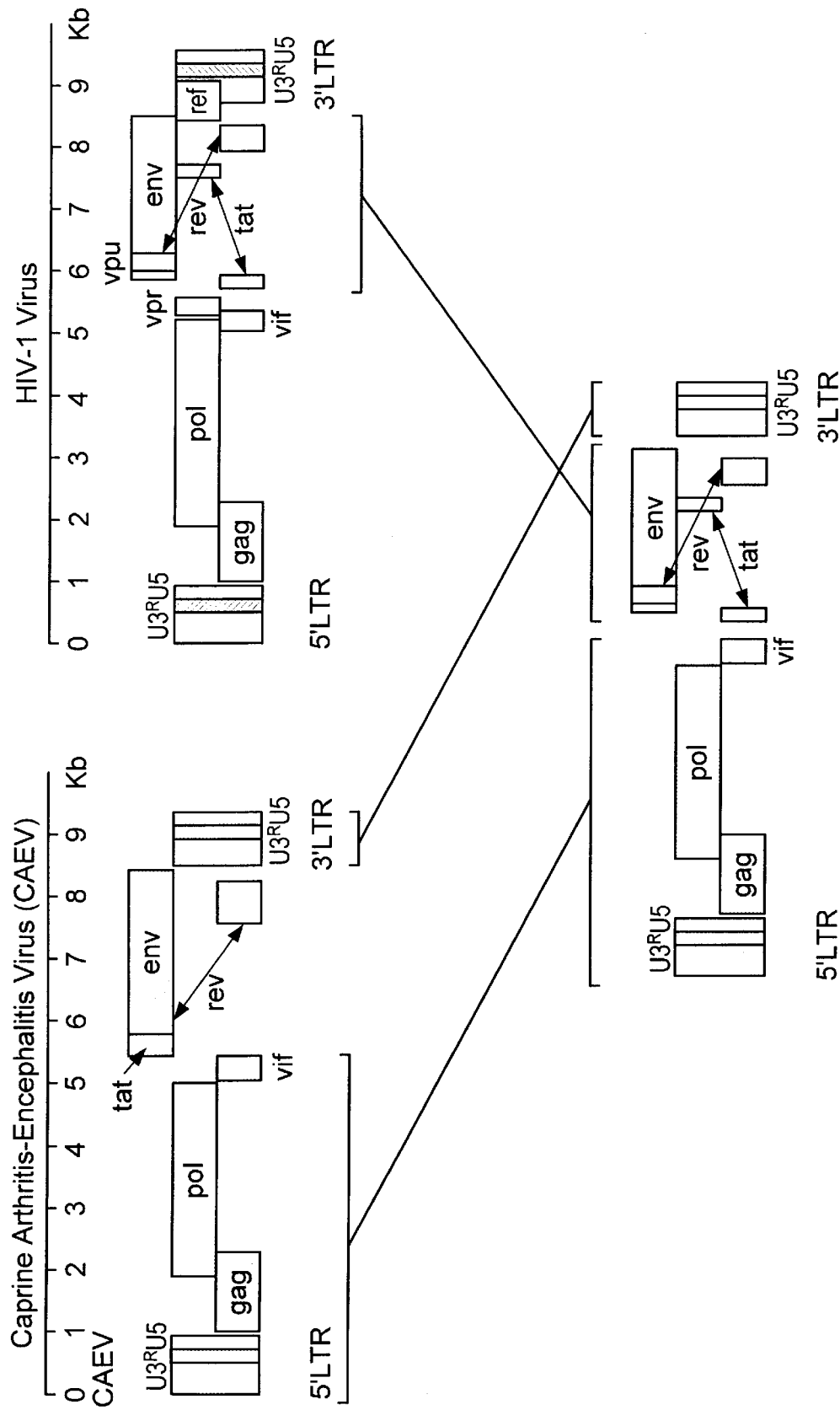
FIG. 1 is a schematic representation of a chimeric CHIV viral genome demonstrating the segments of the CAEV and HIV-1 viral genomes to be used.

The chimeric CAEV/HIV-1 retrovirus ("CHIV") presented herein is a novel approach to developing a live-attenuated AIDS vaccine which has the core of CAEV and the immunogenicity of HIV-1. The advantage to developing a CHIV is that any desired HIV-1 env sequence can in principle be substituted for the CAEV env gene to elicit a more potent and specific immune response.

A precedent for the CHIV exists in recombinant viral chimeras of SIV and HIV-1 (SHIVs). The use of SHIVs has demonstrated that host range, cytopathicity and the specificity of neutralizing antibodies are determined by the envelope sequences (Luciw et al., Proc. Natl. Acad. Sci. 92:7490-7494 (1995)). The development of the SHIV has also shown that genes can be interchanged between lentiviruses (Shibata et al., J. Virol. 65:3514- 3520 (1991)).

CHIV can similarly be used to elucidate relationships between HIV-1 and CAEV genes that have application in vaccine development. Compared to HIV-1, CAEV has a simpler genome in which some corresponding genes (e.g., tat) are not necessary for replication in vivo or in vitro (Harriache et al., J. Virol. 69:5445-5454 (1995)). Thus, replacement of these genes with the corresponding HIV-1 genes can create a viable chimeric retrovirus while increasing and/or broadening the HIV-1 antigenicity of the CHIV.

The present invention also provides a vaccine comprising a CHIV immunogen and a pharmaceutically acceptable carrier. As disclosed herein, vaccination of an individual with a CHIV immunogen evokes an immune response. Vaccination against HIV-1 using a CHIV immunogen provides significant advantages over the use of, for example, a killed or attenuated form of HIV-1 or an HIV-1 protein antigen, in that CAEV is not known to be a human pathogen.

A vaccine of the invention can be administered to an individual not infected with HIV-1 in order to induce an immune response that can decrease the likelihood of infection, or can be administered to an individual already infected with HIV-1 in order to provide a therapeutic response to counter the immunopathology of HIV-1 (see, for example, Cease and Berzofsky, Ann. Rev. Immunol. 12:923-989 (1994)). Thus, a vaccine of the invention can be useful to increase an individual's resistance to HIV-1 infection or to reduce the severity of a pathology due to HIV-1 in an HIV-1 infected individual.

Definitions

As used herein, the term "CHIV immunogen" means a CHIV viral particle, which can be a live, attenuated or killed CHIV, or a polynucleotide expression construct for a CHIV virus. A CHIV immunogen is characterized in that it can stimulate an immune response, either in in vivo or ex vivo. A CHIV viral particle may or may not contain a chimeric viral genome, but does contain at least one CAEV and one HIV-1 viral protein. Preferably the CHIV immunogen stimulates an immune response that is cross-reactive against HIV-1 when administered to a human. Expression constructs for a CHIV retrovirus can be introduced via injection into an individual, as described in U.S. Pat. Nos. 5,561,064, 5,703,055, 5,580,859, and 5,589,466, in order to express immunogenic expression products in vivo.

As used herein, the term "increasing the resistance," when used in reference to HIV-1 infection, means that the likelihood of viral infection or propagation in an individual is reduced due to the stimulation of a cross-reactive immune response against HIV-1 generated by a CHIV immunogen.

As used herein, the term "polynucleotide" refers to all forms of DNA and RNA, whether single-stranded, double-stranded, or higher order. A polynucleotide may be chemically synthesized or may be isolated from a host cell or organism. A particular polynucleotide may contain both naturally occurring residues as well as synthetic residues.

As used herein, the term "expression control segments" refers to polynucleotide segments that can direct the transcription and translation of the recombinant CHIV retrovirus. Such segments include promoters, enhancers, polyA signals, splice donor and acceptor sites, translation start sites, and translation stop sites. Typically the expression control segments for transcription initiation and termination include the long terminal repeat (LTR) regions of a retrovirus, preferably obtained from CAEV or HIV-1.

As used herein, the term "sample," when used in reference to a diagnostic method of the invention, means a tissue specimen, or a fluid specimen, such as blood (which can be whole blood, plasma or serum) or urine, which is obtained from an individual to be tested for CHIV or HIV-1 infection. Methods of obtaining such a sample are well known and routine in the art.

As used herein, the term "TCID $_{50}$" refers to the "tissue culture infectious dose 50%," i.e., the amount of agent required to infect 50% of a population of cultured cells.

As used herein, the term "therapeutically effective amount" means that amount of an immunogen sufficient to stimulate an immune response in the individual undergoing treatment.

As used herein, the term "vaccine" means a composition containing an immunogen which, upon administration to an individual, stimulates an immune response. In particular, a vaccine of the invention contains a CHIV immunogen, which can be administered, for example, to a human, wherein an immune response against CHIV that is cross-reactive against HIV-1 is stimulated. Thus, a CHIV immunogen is useful as a surrogate immunogen for stimulating an immune response against HIV-1.

Construction of the chimeric CHIV retrovirus

The 9.7 kb Co clone is currently the only infectious DNA clone of CAEV (Pyper et al., J. Vir. 58(2):665-670 (1986)). The nucleic acid sequence of CAEV-Co is available as GenBank Accession No. M33677 (see, also, Saltarelli et al., Virology 179:347-364 (1990); Knowles et al., J. Virol. 65:5744-5750 (1991)). However, in principle any variant of CAEV or HIV-1 can be used as a source of material for the chimera of the present invention. Such variants are preferably less than about 15% divergent from known CAEV or HIV-1 sequences as determined by Hamming distance measurement (Faulkner et al., TIBS 13:321- 322 (1988)). Although this divergence is measured at the nucleotide level for isolated strains of CAEV or HIV-1, due to the degeneracy of the genetic code, it would be possible to synthesize polynucleotides that were greater than 15% divergent at the nucleotide level yet code for similar proteins. Thus, a polynucleotide which encodes a protein that can perform the function of a corresponding CAEV or HIV-1 retroviral protein in a recombinant virus and could be encoded by a polynucleotide less than about 15% divergent from a known CAEV or HIV-1 polynucleotide can also be used.

Similarly, the HIV-1 components of the chimera can be isolated from any HIV-1 strain. In particular embodiments, the HIV-1 env coding regions are contributed by either of two strains: $SF_{162}$(macrophage-tropic) or $SF_{33}$ (T-cell-line tropic). Env, or other, HIV-1 coding regions divergent from those described herein can also be used, including those which can mediate infection of both macrophages and T-cells. Divergent HIV-1 genes are less than 15% divergent from a known HIV-1 gene, as described above, or encode a protein which could be encoded by an HIV-1 gene less than about 15% divergent and can perform the function of the encoded HIV-1 protein in a recombinant retrovirus. Furthermore, such a divergent env protein is preferably capable of mediating the infection of human T cells, human macrophages, or both.

The techniques used for manufacturing the chimeric CHIV viruses described herein include the standard techniques for polynucleotide manipulation and propagation. In principle, any technique can be used to generate the chimeric polynucleotide, including chemical synthesis of overlapping oligonucleotides followed by extension and ligation, PCR of desired portions of the individual starting materials using oligonucleotides having complementary 5' extensions that can then be combined in a subsequent PCR, as well as more traditional restriction enzyme digestions to isolate desired segments followed by ligation using linkers and adapters as needed. Additionally, cotransfection into host cells of unligated complementary portions of the viral constructs has been found to result in the generation of intact reproductive virus in the host cells themselves.

The resulting polynucleotide constructs can be propagated using standard techniques. For example, the chimeric viral genome can be inserted into a bacterial vector and propagated in a bacterial host cell, or the virus can be expressed in a mammalian host cell and the resulting viral stock may be serially passaged, or a DNA construct comprising the chimeric viral genome can be propagated in vitro using techniques such as long PCR. The virus can also be propagated in an animal such as a macaque and recovered from a blood sample. Preferably, the polynucleotide constructs are propagated in a manner which maintains the integrity of the created construct, both in terms of the sequence of the polynucleotide as well as the overall structure of the chimeric retrovirus. A preferred manner of propagating the polynucleotide constructs is therefore within a replicating bacterial vector, for example a plasmid, in a bacterial host strain which is defective for recombination, and is preferably rec A-. This inhibits recombination between the direct repeats found in the LTR regions in the chimeric retroviral construct. If recombination does occur in a rec A⁻ bacterial host strain, further recombination-defective strains, known in the art, can be used to propagate such a plasmid construct.

A prototype CAEV/HIV chimera is constructed by molecular substitution of the tat vpu, env and rev genes of HIV-1 into a 9.7 kb infectious clone of CAEV-Co, which retains the gag, pol, vif and LTR functions of CAEV. The rationale for the replacement strategy outlined in FIGS. 3A-C is removal of the CAEV env gene and start sites for the env and rev genes while prematurely terminating the CAEV tat gene with a stop codon. Deletion or stop codon termination of the weakly transactivating CAEV tat gene has no effect on CAEV replication rates in vivo or in vitro (Harmache et al., J. Virol. 69:5445-5454 (1995)). The choice of this option is largely based on the need to preserve the activity of the CAEV vif gene which is required for functional replication (Harmache et al., J. Virol. 69:3247-3257 (1995)) and has an 8 bp out of frame overlap between its termination site and the tat start site.

This CHIV construct relies on the env and rev genes obtained from HIV-1 to perform competently, as both genes are indispensable for CAEV replication. The observation that the CAEV genome contains a rev response element (RRE) comprising a stable stem loop structure similar in location, stability and configuration to that of HIV-1 (Saltarelli et al., Virol. 179(1):347-364 (1990)) is supportive of an analogous role for rev in both CAEV and HIV-1. Therefore this CHIV construct is tested empirically. If necessary, more complex engineering can be performed to incorporate the CAEV rev gene into the chimera. The dispensable nef gene, whose location also overlaps the 3' HIV-1 LTR, is deleted in this CHIV construct.

Additional coding regions may also be incorporated into the CHIV constructs. For example, selectable or detectable markers may be included in the CHIV constructs in order to select or detect expressing cells. Genes encoding immunostimulatory molecules may also be included in order to increase the antigenicity of infected cells and thereby stimulate a stronger immune response.

Furthermore, although the use of replication-competent CHIV constructs and viral stocks is contemplated, replication-defective CHIV constructs and viral stocks are also within the scope of the invention. When introduced into an individual, such constructs produce an abortive infection. Replication-defective CHIV constructs can be prepared as described above, but lack at least one functioning coding region necessary for viral propagation. For example, the viral construct might have a deletion or mutation in a critical gene, and the host cell used would supply the missing function in order to produce a replication-defective viral stock. For instance, the CHIV construct could lack a pol gene, whose function could be supplied by the host cell. The host cell could then produce infectious viral particles incorporating the host cell-produced pol protein, which would permit reverse transcription of the defective RNA retroviral genome into DNA after a viral particle infected another cell. Once that replication-incompetent viral genome had integrated into the infected cell's genome and was expressed, viral antigens could be produced by the infected cell, but the lack of pol protein would prevent subsequent productive infection from occurring. It is also possible to generate chimeric retroviral particles containing CAEV and HIV-1 proteins by expressing coding sequences for those proteins independently in a host cell without the use of a chimeric polynucleotide.

The resulting CHIV construct can be introduced into a mammalian host cell by any technique. Examples of techniques which may be used include transfection, such as calcium phosphate transfection, lipofection, encapsulation in artificial viral envelopes, electroporation, scraping or rubbing methods, and bolistic impact. Once viral particles containing the construct have been generated, viral infection may also be employed in cells expressing the appropriate viral receptors.

Mammalian host cells useful in the invention include those which are able to express introduced CHIV constructs, as well as those cells which are able to undergo infection by the CHIV viral particles produced. Host cells can be established cell lines or primary isolates. For example, CHIV constructs can be introduced into primary goat synovial membrane (GSM) cells, prepared by techniques known in the art, or into a human rhabomyosarcoma cell line, for example the cell lines RD (ATCC #CCL-136) or RD-5 (Luciw et al., Proc. Natl. Acad. Sci. 92:7490-7494 (1995)). Further examples of mammalian host cells which may be employed include primary human and macaque PBMC and macrophages, prepared by known techniques, and the CD4+ cell lines HUT78 (Marchalonis et al., Cell Immunol. 77(1):161-75 (1983); ATCC #TIB-161) and CEMX174 (Sei et al. Cell Immunol. 125(1):1-13 (1990)).

The host cells can be analyzed to detect functioning of the introduced construct. Assays that can be performed include: (a) immunoassays to detect production of gp120 (by gp120 antigen capture ELISA) and the CAEV gag protein p28 (by Western blot using polyclonal goat sera); (b) CAEV gag and HIV-1 env PCR of the GSM or RD-5 genomic DNA to detect proviral DNA sequences; and (c) CAEV gag and HIV-1 env RT-PCR of total cellular RNA.

The viability of the complete CHIV construct is tested by transfection into a suitable host cell, for example GSM cells, or alternatively the human rhabdomyosarcoma line RD-5 (Luciw et al., Proc. Natl. Acad. Sci. 92:7490-7494 (1995)). Supernatants are monitored by reverse transcriptase (RT) assay and CAEV- and HIV-RT-PCR. The host-cell range of the generated chimeras can be analyzed by inoculation into human and rhesus macaque PBMC and macrophages, and HUT78 and CEMX 174 cell lines, followed by tests for viral replication (RT-PCR and RT assay). The production of HIV-1 env and CAEV gag proteins can be assayed by gp120 antigen capture ELISA and CAEV p28 Western blot. Based on the tropism of the HIV-1 strain from which the envelope gene is derived, the tropism of the CHIV chimera can be predicted.

For example, the $CHIV_{SF33}$ chimera is predicted to replicate in the HUT78 and CEMX174 lines, which support the expression of T-cell-line-tropic HIV-1 strains. The $CHIV_{SF162}$ chimera is predicted to grow in human, macaque and GSM cell cultures. Expression of chimeric genes in the cultures is evaluated by RT assays and by RT-PCR for CAEV gag and HIV-1 env. In addition, sequencing of RT-PCR products can be performed to confirm the identity of the expressed genes. Cultures are examined for syncytium formation or cytopathicity by microscopic observation. Syncytia are giant multinucleate cells characteristic of productive retroviral infection. Cytopathicity can be determined by syncytium formation as well as cytoplasmic vacuolization or cell death. It is desirable that the CHIV form syncytia in or are otherwise cytopathic towards the intended target cells in vitro, as there is no host immune system to combat the infection. Preferably the CHIV produces such a cytopathic effect in a large proportion of such cells.

Viral protein production is monitored by immunologic methods as in the transfection experiments, and if necessary, by immunoprecipitation of radiolabeled cultures, labeled for example with $^{35}$S-methionine.

If proviral DNA and cellular RNA are detected in the absence of protein, the possibility of abnormal splicing of one or more gene functions will be analyzed by Northern blotting. Cryptic splice sites that are inadvertently activated in the chimera can be removed by standard techniques such as site-directed mutagenesis or mutagenic PCR. Strong consensus splice sites can be introduced by similar techniques where necessary to improve the utilization of desired splice sites. Alternatively, internal ribosome entry sites may be introduced into the construct in order to directly promote the translation of a desired protein.

If proteins are detected in the cells, but no mature viral particles are formed, an assembly problem may exist. In HIV-1 assembly, nascent envelope molecules are targeted to matrix protein (MA) sites which are myristylated, a mechanism which is unknown in ungulate lentiviral assembly (Dorfman et al., J. Virol. 68(3):1689-1696 (1994)). However, incompatibility due to a lack of myristylation can be corrected by supplying a myristylated membrane-binding domain from another virus (Wills et al., J. Virol. 65(7):3804-3812 (1991)).

Finally, if no integrated chimeric DNA is detected, a reporter gene such as bacterial chloramphenicol acetyltransferase (CAT) can be used to evaluate the role of the tat gene in CAEV-Co (Saltarelli et al., Virology 197(1):35-44 (1993)). The CAT gene can be placed under the control of the CAEV-Co LTR promoter, and constructs with and without the CAEV tat gene are evaluated for expression in the host cell. If CAT is expressed in the host cell but the CHIV is not, then additional CAEV genes can be incorporated into the CHIV as necessary to permit viral replication.

Figure 3A:
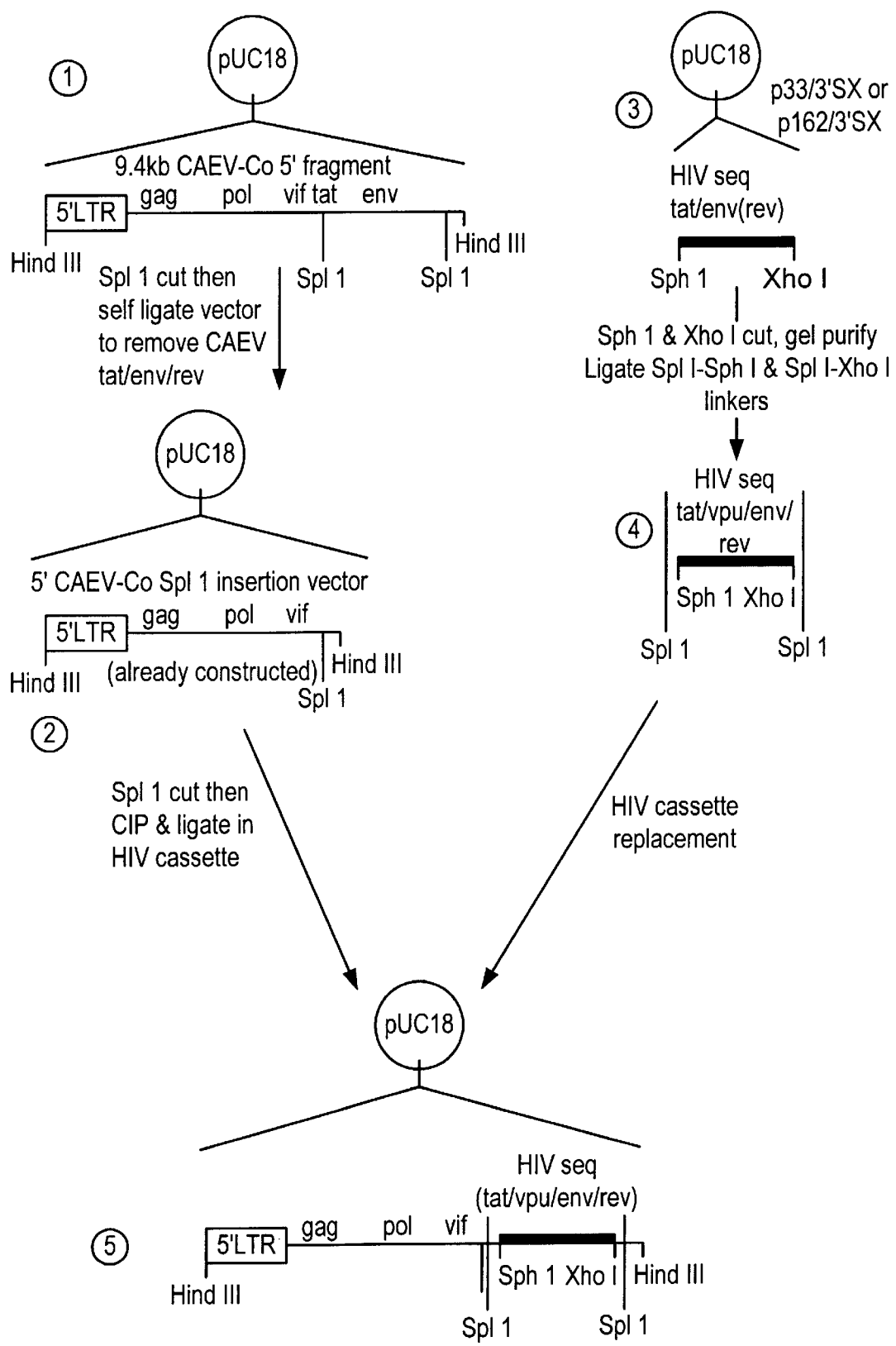
FIG. 3A shows a detailed strategy for preparing segments of the HIV-1 and CAEV genomes for incorporation into a CHIV.
Figure 3B:
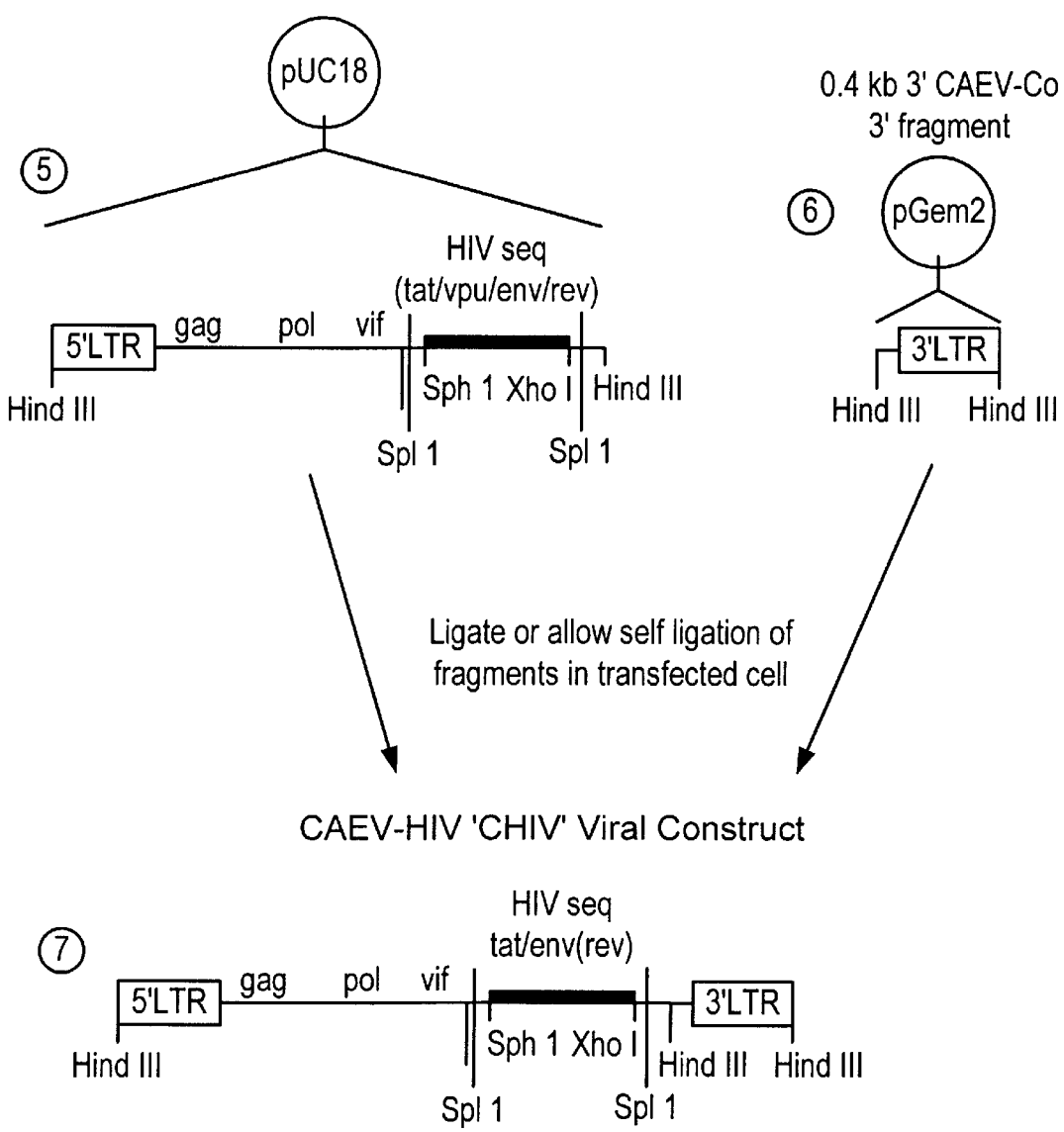
FIG. 3B shows a detailed strategy for incorporating the 3' LTR region of CAEV-Co along with the segments shown in FIG. 3A to produce a complete CHIV viral construct.
Figure 3C:
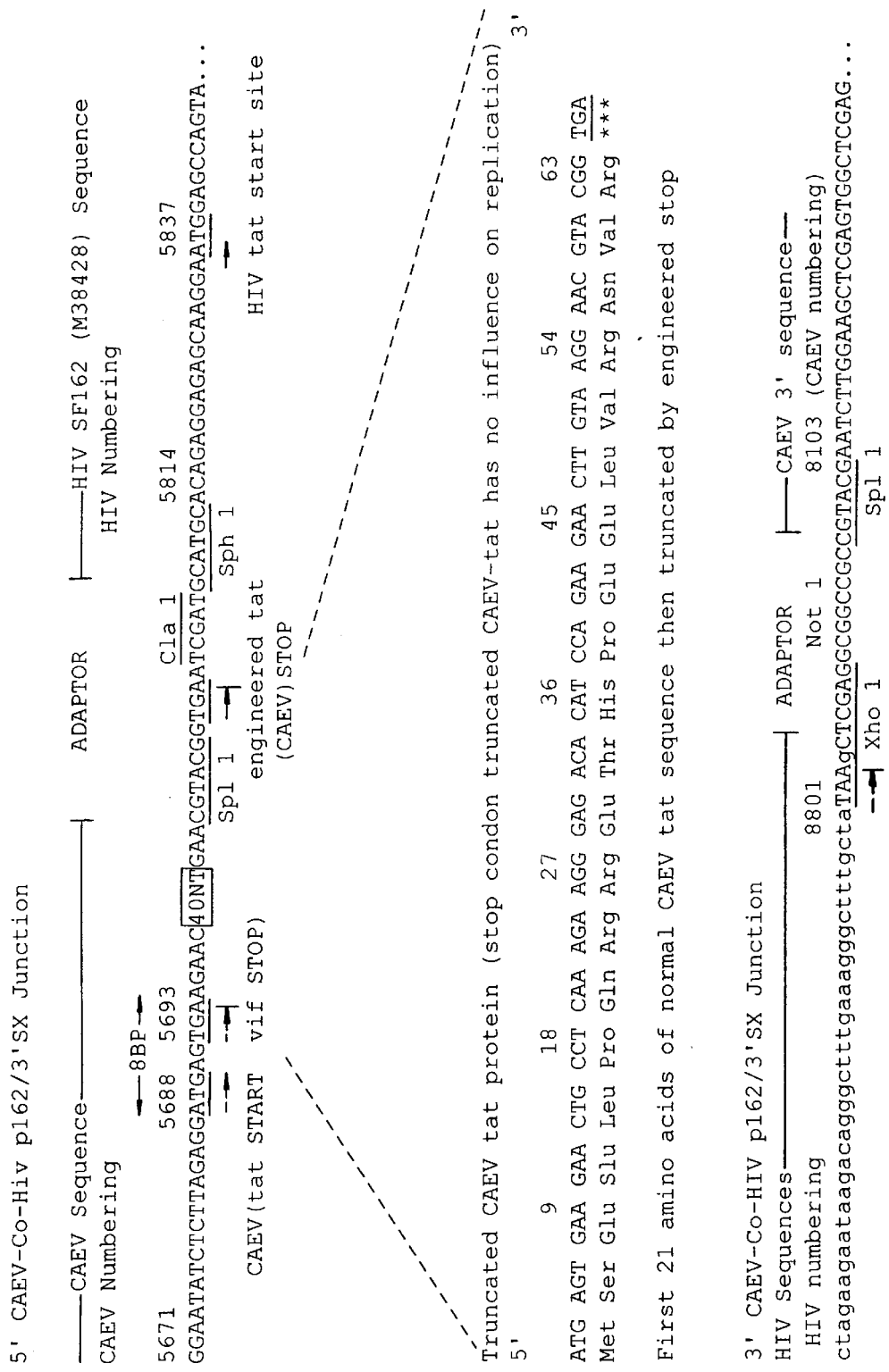
FIG. 3C shows details of the nucleotide sequence of the junctions between CAEV- Co and HIV-1 segments in the CHIV shown in FIG. 3B, along with the coding region of the truncated CAEV tat protein. Shown are the 5' CAEV-Co/HIV p162/3' SX junction (SEQ ID NO: 1), the truncated CAEV tat protein sequence (SEQ ID NO: 2), and the 3' CAEV- Co/HIV p162/3' SX junction (SEQ ID NO: 3).

Based on the results of this diagnostic approach, modifications to the construct presented in FIGS. 3A-C are made. Additional coding regions from CAEV and/or HIV-1 can be incorporated into the chimera in order to obtain a better functioning retrovirus. Coding regions negatively affecting the chimera can be deleted.

The result is a chimeric retrovirus that: comprises at least the envelope gene from an HIV-1 strain; comprises sufficient CAEV sequences to attenuate the biological effects of the recombinant virus in a primate so as to render the CHIV nonpathogenic; has the remainder of the viral genome derived from either CAEV or HIV-1; is able to replicate in vitro in a host cell; and produces an immune response against HIV-1.

A viral stock containing CHIV viral particles can be generated from an expressing host cell using standard techniques. For example, the culture supernatant from a $^3$H-uridine labeled host cell culture expressing CHIV can be subjected to sucrose density gradient centrifugation. The location of the retroviral particles can be determined by collecting fractions from the gradient and assaying for radioactivity and reverse transcriptase activity. More directly, a culture expressing CHIV can be centrifuged at 130,000× g to pellet the viral particles. The resulting pellet can be washed and repelleted, if desired, and resuspended in an appropriate solution.

Where the viral particles are to be introduced into a primate, the virus should be passaged in host cells derived from that primate in order to avoid nonspecific immune responses to host cell antigens. For example, where the viral particles are to be introduced into a human, the virus is preferably propagated in human PBMC in order to avoid immune responses to nonhuman host cell antigens inadvertently packaged in the viral particles.

An animal model can be used to further evaluate the CHIV prior to use in humans. In vivo infection can be performed in an animal, for example a macaque, to determine if the CHIV is pathogenic, and if HIV-1 strain-specific immune responses develop to the HIV-1 envelope. The animal can be transfused with a viral inoculate produced as described above. Blood can be collected at regular intervals in order to determine whether infection has occurred and whether pathogenic changes in the animal's blood cell counts have occurred.

Where the CHIV immunogen comprises a polynucleotide containing a CHIV viral genome, the polynucleotide can be prepared by techniques known in the art for preparation of polynucleotide vaccines. For example, the methods described in U.S. Pat. Nos. 5,561,064, 5,703,055, 5,580,859, and 5,589,466 can be used to prepare polynucleotides suitable for administration to a mammal in order to generate an immune response.

A vaccine of the invention preferably contains, in addition to a CHIV immunogen, a pharmaceutically acceptable carrier. Pharmaceutically acceptable carriers are well known in the art and include solutions such as physiologically buffered saline or other solvents or vehicles such as glycols, glycerol, oils, for example olive oil, or injectable organic esters. If desired, a vaccine of the invention can contain a pharmaceutically acceptable carrier that is an adjuvant. Adjuvants such as aluminum phosphate, aluminum hydroxide, Freund's complete or incomplete adjuvant, QS21 (described in U.S. Pat. No. 5,889,176, Rovinski et al.) or other proprietary adjuvants are known in the art and commercially available (Ribi Immunochem Research, Inc., Hamilton MT). The addition of an adjuvant generally decreases the amount of a CHIV immunogen required to stimulate an immune response.

A pharmaceutically acceptable carrier also can contain a physiologically acceptable compound that acts, for example, to stabilize the CHIV immunogen or increase its absorption. Physiologically acceptable compounds include, for example, carbohydrates, such as glucose, sucrose or dextrans; antioxidants, for example ascorbic acid or glutathione; chelating agents; low molecular weight proteins; or other stabilizers or excipients. One skilled in the art would know that the choice of a pharmaceutically acceptable compound, including a physiologically acceptable compound, depends, for example, on the route of administration of the vaccine and on the particular physio-chemical characteristics of the CHIV immunogen.

A CHIV immunogen can be immunogenic by itself, can produce immunogenic molecules in vivo, or can be attached to a carrier molecule such as bovine serum albumin or an inert carrier such that the CHIV immunogen-carrier complex can stimulate an immune response (see, for example, Harlow and Lane, Antibodies: A laboratory manual, Cold Spring Harbor Laboratory Press, 1988). For example, where a vaccine contains CHIV viral particles, the virus is immunogenic and can stimulate an immune response in a vaccinated individual.

Methods for vaccinating an individual so as to stimulate an immune response also are well known (Harlow and Lane, supra, 1988). The immunogen can be administered, for example, intravenously, intradermally, subcutaneously, orally, anally, vaginally, intranasally or transdermally. The vaccine is formulated taking into consideration the intended route of administration. In addition, it can be advantageous to administer one or more booster immunizations. The need to administer a booster immunization and the timing of such booster immunizations can be determined empirically by measuring, for example, the presence and titer of anti-HIV-1 antibodies in a vaccinated individual's serum.

Although reference is made herein to the administration of a CHIV immunogen to an individual, it is recognized that an immune response against HIV-1 can be stimulated in vivo or ex vivo. For example, it can be desirable to stimulate an immune response against HIV-1 ex vivo where the individual to be treated has AIDS or is infected with HIV-1. For ex vivo stimulation, lymphocytes are removed from the individual and immunized in culture. Simultaneously, the lymphocyte population can be expanded. These stimulated, expanded immune cells can then be infused into the individual, thereby providing a therapeutic advantage. Such a treatment can be palliative and can increase the quality of life of an individual suffering from AIDS.

The amount of a CHIV immunogen that constitutes a therapeutically effective amount can vary depending, for example, on whether stimulation of the immune response is in vivo or ex vivo, whether the administration is a first administration or a booster administration, whether an adjuvant is administered with the immunogen, and, when administered in vivo, on the route of administration and the weight of the patient. Methods for determining a therapeutically effective amount of an immunogen are routine and well known in art (see Powell and Newman, Vaccine Design: The subunit and adjuvant approach (Plenum Publ. Corp.; 1994)).

For example, where CHIV viral particles are administered to a monkey, a therapeutically effective amount of the particulate CHIV immunogen can be in the range from about 0.1 to about $1 \times 10^8$ TCID$_{50}$, usually from about $7 \times 10^2$ to about $7 \times 10^4$ TCID$_{50}$. Where CHIV viral particles are administered to a human, a therapeutically effective amount of the particulate CHIV immunogen can be in the range from about 0.1 to about $1 \times 10^8$ TCID$_{50}$, usually from about $5 \times 10^3$ to about $5 \times 10^5$ TCID$_{50}$. Where the immunogen is a polynucleotide comprising a single complete CHIV retroviral genome, a therapeutically effective amount can be in the range of from about 0.05 µg/kg to about 50 mg/kg, usually from about 0.005 to about 5 mg/kg.

Samples can be taken from an individual who has received a CHIV immunogen and can be tested to determine if the individual has produced an immune response to the immunogen, for example to determine if the individual has produced antibodies to HIV-1. Methods for detecting an antigen-antibody interaction present in a sample are well known in the art and include, for example, the use of a detectably labelled antigen or the use of a detectably labelled secondary antibody, which is an antibody that specifically binds a particular class of antibody such as IgG, IgA, IgM, IgD or IgE from a particular mammalian species (see, for example, Green and David, U.S. Pat. No. 4,376,110, issued Aug. 1983, which is incorporated herein by reference). For example, if a sample is a blood serum or blood plasma sample from a human individual, a secondary antibody can be a goat anti-human IgG. Such secondary antibodies can be prepared using well known methods or can be purchased from a commercial source. Methods for detectably labeling a CHIV antigen or an antibody also are known in the art.

The following examples are intended to illustrate but not limit the present invention.

EXAMPLE I

Generation of a Chimeric CAEV/HIV-1 Retrovirus

The experimental design is based on the infectious clone CAEV-Co, into which the env functions of HIV-1 are substituted. A detailed outline for substituting the HIV-1 env functions derived from strains SF$_{162}$ (Cheng-Mayer et al., J. Virol. 64(8):4012-4020 (1990) and SF$_{33}$ (York-Higgins et al., J. Virol. 64(8):4012-4020 (1990)) into CAEV-Co is presented in FIGS. 3A-C. To make a CAEV/HIV (CHIV) construct, the 5' 9.4 kb HindIII fragment of CAEV is modified by deleting portions of the tat/env/rev genes needed for expression, which are then replaced with the HIV-1 tat/vpu/env/rev genes. This modification is shown in FIG. 3A, steps 1-5.

The pUC 18 and pGem2 vectors containing the 9.4 kb 5' and 0.4 kb 3' CAEV-Co segments (Pyper et al., J. Virol. 58(2):665-670 (1986), respectively, were obtained from Dr. J. Clements (Johns Hopkins University) and transformed into the rec A– bacterial host DH5α. Selected clones were maxiprepped using standard SDS-NaOH lysis, high salt precipitation to remove bacterial DNA and debris and isopropyl alcohol precipitation. RNase and proteinase K treatment of redissolved plasmid DNA was followed by phenol chloroform extraction, ethanol precipitation and resuspension in TE buffer. Both plasmids were subjected to restriction digestion and partial sequencing to confirm identity.

The 5' CAEV-Co 9.4 kb insert in pUC18 shown in FIG. 3A as construct 1 has unique Spl 1 sites at 5745 and 8097. The Spl 1-Spl 1 piece contains most of the CAEV tat gene as well as the start sites and most of the coding regions for the env and rev genes. This piece can be deleted by digesting construct 1 with Spl 1 and religating the cut plasmid to form a single Spl 1 insertional site 5' CAEV plasmid designated in FIG. 3A as construct 2. The unexcised regions of the 3' distal env and rev genes (including the Tm region of env) do not have translation start sites, and therefore should not be translated. Additionally, the CAEV tat gene is prematurely terminated while substituting an HIV-1 tat sequence (described below).

Two alternate HIV-1 cassette inserts, each containing complete HIV-1 tat, vpu, env, and rev genes, are derived from the plasmid constructs p33/3'SX and p162/3'SX (Luciw et al., Proc. Natl. Acad. Sci. 92:7490-7494 (1995)), containing respectively the SF$_{33}$ (York-Higgins et al., J. Virol. 64(8):4012-4020 (1990) and SF$_{162}$ (Cheng-Mayer et al., J. Virol. 64(9):4390-4398 (1990)) env genes, which are schematically shown in construct 3 of FIG. 3A. These plasmids have been constructed with 5' Sph 1 and 3' Xho 1 sites flanking the HIV-1 tat/vpu/env/rev insert. These Sph 1-Xho 1 fragments are excised and specific terminal adaptor sequences that both end in a Spl 1 site which is not present in the HIV-1 constructs are ligated. The DNA junction sequences are described in FIG. 3C.

In the final step in constructing the 5' CAEV-HIV construct, the Spl 1 terminated HIV-1 insert(s) 4 are ligated into the Spl 1 cut insertional vector 2. The efficiency of this operation can be insured by first removing the 5' overhanging phosphate groups of the insertional vector 2 with calf alkaline phosphatase (CIP) to prevent self closure of the vector.

As shown in FIG. 3B, the complete CAEV-HIV clone is assembled by ligating the Hind III fragments from the final 5' construct 5 with the Hind III fragments of the 0.4 kb CAEV fragment 6 that contains the 3' CAEV LTR. Alternatively, the two fragments can be introduced together into GSM cells, where the two fragments can self-ligate. The final result of this ligation is the CAEV-HIV 'CHIV' viral construct 7.

The details of the Spl 1 DNA adaptors at the 5' CAEV/HIV and 3' HIV/CAEV junctions are shown in FIG. 3C. The 5' CAEV-HIV junction shows the 8 bp out of frame overlap of the CAEV vif and tat genes (5688-5693) which required the design of a CAEV tat 'in frame' stop codon (TGA) in the adaptor region. The DNA and 21 amino acid sequences of the truncated CAEV tat gene, from the start site to the termination codon, are shown immediately below. The Sph 1 restriction site in the p162/3'SX plasmid (5814) is shown along with the continuing sequence of HIV-1 162 to just past the HIV-1 tat start site. Also designed into the 5' Spl 1 adaptor is a unique Cla 1 site (ATCGAT) that is not present in either the CAEV plasmids or the HIV-1 insert (to be used with a Not 1 site, described below).

The 3' HIV-CAEV junction DNA sequence is also shown in FIG. 3C with the HIV-1 Xho 1 site and the adaptor/CAEV Spl 1 site, as well as the HIV-1 env gene stop site (8801). Also included in the 3' Xho 1-Spl 1 adaptor is a unique Not 1 site (GCGGCCGC) that is absent from the CAEV clones and the HIV-1 insert. The Not 1 site, along with the Cla 1 site in the 5' adaptor, allows replacement of this HIV-1 DNA cassette in a 5' Cla 1-3' Not 1 directional specific manner.

The rationale for the replacement strategy outlined in FIGS. 3A-C is removal of the CAEV env gene and start sites for the env and rev genes while prematurely terminating the CAEV tat gene with a stop codon. Deletion or stop codon termination of the weakly transactivating CAEV tat gene has no effect on CAEV replication rates in vivo or in vitro (Harmache et al., J. Virol. 69:5445-5454 (1995)). The choice of this option was largely based on the need to preserve the activity of the CAEV vif gene which is required for functional replication (Harmache et al., J. Virol. 69:3247-3257 (1995)) and has an 8 bp out of frame overlap between its termination site and the tat start site.

This CHIV construct relies on the env and rev genes supplied by HIV-1 to perform competently, as both genes are indispensable. The observation that the CAEV genome contains a rev response element (RRE) comprising a stable stem loop structure similar in location, stability and configuration to that of HIV-1 (Saltarelli et al., Virol. 179(1):347-364 (1990)) is supportive of an analogous role for rev in both CAEV and HIV-1. Therefore this CHIV construct is tested empirically. If necessary, more complex engineering can be performed to incorporate the CAEV rev gene into the chimera. The dispensable HIV-1 nef gene, whose location also overlaps the 3' HIV-1 LTR, is deleted in this CHIV construct.

EXAMPLE II

Expression of Recombinant Retroviruses in Host Cells

The viability of the complete CHIV construct is tested by transfection into GSM cells or the human rhabdomyosarcoma line RD-5 (Luciw et al., Proc. Natl. Acad. Sci. 92:7490-7494 (1995)). Transfected and mock transfected culture supernatants are tested for viral production by CAEV gag and HIV-1 env RT-PCR and by RT assay. A step-by-step analysis of transfected cells is performed to detect functioning of the construct, including: (a) immunoassays to detect production of gp120 (by gp120 antigen capture ELISA) and the CAEV gag protein p28 (by Western blot using polyclonal goat sera); (b) CAEV gag and HIV-1 env PCR of the GSM or RD-5 genomic DNA to detect proviral DNA sequences; (c) CAEV gag and HIV-1 env RT-PCR of total cellular RNA.

Figure 2A:
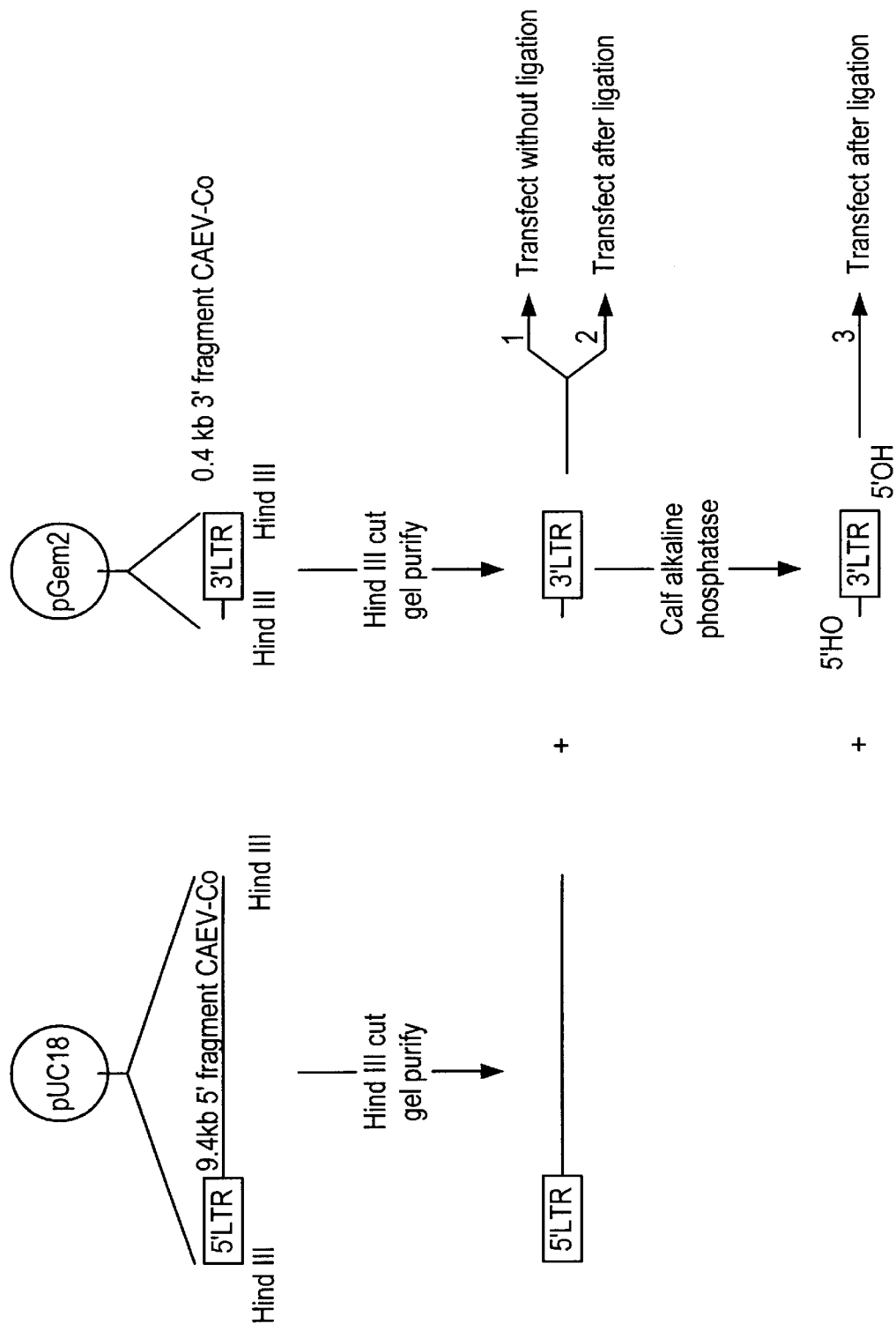
FIG. 2A demonstrates the scheme used to prepare segments of the CAEV-Co viral genome for incorporation into the CHIV.
Figure 2B:
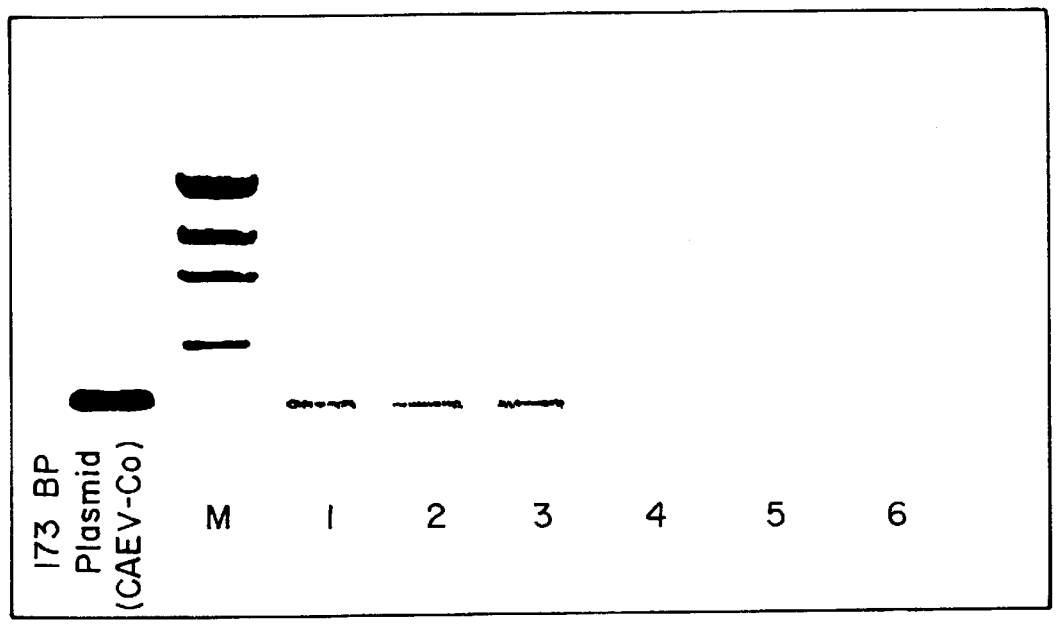
FIG. 2B shows the detection by RT-PCR of CAEV-Co sequences in the culture supernatant of cells expressing CAEV-Co after introduction of the ligated and unligated segments produced in FIG. 2A.

FIGS. 2A-B shows that the two CAEV fragments comprising the CAEV-Co genome, a 9.4 kb 5' fragment in pUC18, and a 0.4 kb 3' fragment in pGem2, will produce live virus when transfected into GSM cells. GSM cells were Lipofectamine transfected with either: (1) unligated 5' and 3' fragments, or ligated DNA without (2) or with (3) calf alkaline phosphatase treatment, as shown in FIG. 2A. All three modalities resulted in viral production as determined by CAEV gag RT-PCR of culture supernatants (FIG. 2B). Thus in transfecting GSM cells with the 5' and 3' fragments of the chimera, pre-ligation may not be necessary. Mock transfected GSM cultures, lanes (4), (5) and (6) were PCR negative.

Methods:

The CAEV-Co 9.4 kb (5' clone) and 0.4 kb (3' clone) plasmids were separately digested with Hind III and the fragments were gel purified to obtain preparative quantities. The fragments were ligated, with and without phosphatase treatment of the smaller fragment, or were transfected without ligation. Transfection into GSM cells was performed using Lipofectamine (BRL) following the conditions of the manufacturer. After 12 hours, in Optimem/Lipofectamine/DNA reagents, GSM cultures were washed in DMEM several times, and returned to standard tissue culture conditions of DMEM containing 5% fetal calf serum at 37° C and 5% $CO_2$.

Six days post transfection, supernatant aliquots were extracted with triazol (BRL) and CAEV gag nested RT-PCR was performed, amplifying a 173 bp sequence. Transfected cells which received both fragments, whether phosphatase treated or ligated, produced an amplified 173 bp fragment from the extracted supernatant.

Transfection of the CHIV constructs into GSM or RD-5 cells is similarly performed, and the culture supernatant is assayed for production of recombinant chimeric virus.

EXAMPLE III

Determination of the Host Range of CHIV

The host cell range of viable chimeras is determined as described by Luciw et al. (Luciw et al., Proc. Natl. Acad. Sci. 92:7490-7494 (1995)) by inoculation of the following cell cultures with a CHIV viral stock, produced by transfected cells as described above or by subsequent passage therefrom, and which may be concentrated if necessary: human and macaque PBMC and macrophages, GSM cells, and the CD4+ cell lines HUT78 and CEMX174. Serial dilutions of the viral stock may be used to inoculate the cultures, and amount of virus used typically can range from about 0.1 to about $1\times10^6$ $TCID_{50}$. Expression of chimeric genes in the cultures is evaluated by RT assays and CAEV gag and HIV-1 env RT-PCR as in the transfection experiments. In addition, RT-PCR products are sequenced to confirm the identity of the expressed genes. Viral protein production is monitored by immunologic methods as in the transfection experiments, and if necessary, by immunoprecipitation of radiolabeled culture supernatants or lysates, labeled for example with $^{35}$S-methionine. Cultures are examined for syncytium formation or cytopathicity by microscopic observation.

In vitro propagation of CHIV in macaque PBMC:

PBMC are prepared from 10 ml of blood from two naive macaques and plated in 6-well microtiter plates (Falcon), $3 \times 10^6$ cells/well in RPMI, 10% fetal calf serum and 10 μg/ml PHA. After 24 hrs, 0.5 ml of viral inoculate or medium are added per well. Cultures are harvested after 4 days and cells and supernatants are separated and extracted with Trizol for nested gag RT-PCR.

In vitro propagation of CHIV in human PBMC:

PBMC are prepared from a CAEV- and HIV-1-negative human donor by Ficoll density centrifugation. PBMC are added to 24-well microtiter plates (Falcon 3047), $0.8 \times 10^6$ cells/well in RPMI, 10% human AB serum and 10 pg/ml PHA. After 24 hours, 200 μl of viral inoculate is added. After 4 additional days, the cultures are harvested and the cells and supernatants are separated by centrifugation. Cells are washed 3× in PBS, pH 7.4. Genomic DNA, cellular RNA and supernatant RNA extractions, and PCR and RT-PCR are performed using nested CAEV gag primers as described above.

Detection of reverse transcriptase activity produced by viral passage:

PHA stimulated human PBMC from a PCR (−) donor are plated in 24 well microtiter plates, and are inoculated with the CHIV viral inoculate ($10^5$ TCID$_{50}$/well). Simultaneously, cell free aliquots of the CHIV viral inoculate are placed in the CO$_2$ incubator. Aliquots of culture supernatants are collected on days 0, 2 and 6, and RT assays are performed as described (Cheng-Mayer et al., J. Virol. 64(9):4390-4398 (1990)). Briefly, 15 μl cell free supernatant is aliquoted into duplicate 96 well plates and mixed with 50 μl $^{32}$P-TTP and a cocktail containing 50 mM Tris, pH7.8, 75 mM KCl, 2 mM DTT, 5 mM MgCl$_2$, 5 μg/ml poly-A template, 6.2 μg/ml oligo dT 12-18 primer, 0.05% NP40, 0.5 mM EGTA, and 10 μCi/ml $^{32}$P. The plates are incubated in a humidified chamber at 37° C. for 1.5-2 hours, and then 10 μl from each well is dotted onto CD81 filter paper and air dried for 30 minutes. The filter is then washed 5 times with 1× SSC and once with ethanol. Radioactive incorporation is measured quantitatively using a Phosphor Imager™.

EXAMPLE IV

Preparation of a CHIV Virus Stock

The culture supernatant from a $^3$H-uridine labeled CHIV-producing host cell culture is subjected to sucrose density gradient centrifugation. The location of the retroviral particles are determined by collecting fractions from the gradient and assaying for radioactivity and reverse transcriptase activity. Alternatively, the cultures may be unlabeled, and immunological methods can be used to identify fractions containing viral proteins.

EXAMPLE V

An Animal Model for CHIV Infection

In vivo infection in macaques is performed to determine if the CHIV is pathogenic, 5 and if HIV-1 strain-specific immune responses develop upon CHIV infection. Pathogenicity is determined by a precipitous drop in the cell count of the cell type which the virus infects.

Pathogenicity can be evidenced by rising levels of viremia, which may result in Coomb's positive hemolytic anemia or thrombocytopenia. Pathogenicity can also be demonstrated by clinical signs such as weight loss or enlargement of peripheral nodes. A CHIV demonstrating such pathogenicity can be reengineered by substituting additional CAEV sequences for corresponding HIV-1 sequences in the CHIV.

Methods:

A healthy adult macaque is transfused via femoral vein with 10 ml of a CHIV viral inoculate containing from about $7 \times 10^2$ to about $7 \times 10^4$ TCID$_{50}$, preferably about $7 \times 10^3$ TCID$_{50}$. Blood collections are obtained from the macaque approximately at 4 week intervals for PBMC isolation and RT-PCR. Nested gag and env RT-PCR of cellular RNA are performed as described above.

EXAMPLE VI

Use of a CHIV Vaccine to Vaccinate an Individual

This example describes a method of administering a CHIV vaccine to an individual in order to stimulate an immune response.

CHIV virus is prepared by inoculation of a host cell as described above. Cell supernatants are harvested and CHIV virions are pelleted by centrifugation at 150,000× g at 4° C. to obtain a sterile suspension of approximately $2 \times 10^8$ pfu/ml, containing 50% glycerol as a diluent (see Graham et al., J. Infect. Dis. 166:244-252 (1992)). Recipients of live virus are vaccinated intradermally, using a sterile bifurcated needle, with 50 μl CHIV suspension to a single skin site. Vaccinations also can be performed using a killed or attenuated CHIV preparation or other CHIV immunogen, for example a DNA construct containing the CHIV viral genome. A sterile transparent dressing is applied to the vaccination site, then removed after a crust is formed.

Blood samples are drawn on or about days 14, 28 and 54 after administration of the CHIV immunogen and evaluated to determine antibody titers (humoral response) or T helper or cytotoxic T cell immune response (cellular response). Methods for examining the humoral and cellular responses are well known in the art (see, for example, Egan et al., J. Infect. Dis. 171:1623-1627 (1995); see also, Harlow and Lane, supra, 1988). If desired, a secondary (booster) immunization is administered on or about day 56 after the initial vaccination. Additional evaluations of humoral and cellular responses are made on or about days 70, 90, 160, 180, 270 and 355 after the initial vaccination. If desired, a tertiary (booster) immunization is administered on or about day 365 or subsequently as needed. The production of HIV-1 env and CAEV gag proteins in the individual can be assayed from the blood samples by gp120 antigen capture ELISA and CAEV p28 Western blot.

EXAMPLE VII

Detection of Neutralizing Antibodies in Humans Inoculated with CHIV

This example describes the methods used to demonstrate that CHIV infected individuals generate an immune response to CHIV antigens.

Blood Samples and Reagents:

Human and goat blood samples are collected and the serum component is used for immunologic testing. The antigens used in the ELISA and western blot assays to measure levels of serum antibodies include crude CHIV and CAEV, as well as recombinant HIV-1 gp120 and p24 purchased from Intracel (Shepreth UK).

The CHIV virus is produced from an expressing host cell culture, such as GSM or RD-5 cells, as described above. Medium of CHIV infected cultures is collected and clarified by centrifugation at 600× g. Aliquots of the crude CHIV preparation can be stored frozen at −70° C. The crude CHIV preparation can be used to isolate purified CHIV or can be used to prepare purified proteins.

HIV-1 ELISA and Western Blot Assays:

Certified HIV-1 and Western blot diagnostic kits are purchased from Organon Teknika (Cambridge UK) and the assays are performed as recommended by the supplier.

ELISA and Western blot assays are performed using the individual recombinant HIV-1 antigens, gp120 and p24, and HRP-conjugated rabbit anti-goat and goat anti-human second antibodies (Zymed Laboratories Inc.) as previously described (Douvas and Takehana, AIDS Res. Hum. Retrovir. 10:253-262 (1994); Crow et al., Cell. Immunol. 121:99-112 (1989)).

HIV-1 Viral Neutralization Assay:

Virus neutralization assays are performed in 48 well tissue culture plates using PHA-activated normal donor PBMC maintained in growth medium at a concentration of $1\times10^6$ cells/ml as targets for infection. Various dilutions of HIVIG™, heat-activated (56° C., 30 min) sera or purified IgG are incubated with 10 or 50 $TCID_{50}$ of virus for 30 min at 37° C.

Negative controls for the sera and for HIVIG™ include heat inactivated serum from individuals not infected by HIV-1 and not affected by a systemic rheumatic disorder, and IVIG™, respectively. HIVIG™, which is a neutralizing IgG preparation from pooled serum from 9 seropositive donors in early stages of HIV-1 infection, and IVIG™, which is IgG from normal donors, are obtained from North American Biologicals Inc. (Miami FL). Alternatively, other sources of HIV-1 neutralizing antibodies and control antibodies can be used. $TCID_{50}$ is determined using routine methods of viral titering.

Following incubation of the serum or IgG with the virus, serum/IgG-virus mixtures are added to the target cells in triplicate. After an overnight incubation at 37° C., the plates are centrifuged at 1000 rpm for 5 min and the medium is completely replaced. This washing step is repeated 3× to ensure complete removal of the serum/IgG-virus inoculum. On day 4 of culture, the medium is changed and on day 7 the supernatant is harvested for quantitation of p24 core antigen. Percent inhibition is determined by comparing the mean p24 core antigen concentration in each serum/IgG treated tissue culture well with that of the specific negative control.

In parallel, a control is prepared to measure any non-specific reduction in the amount of p24 core antigen measured due to a serum or HIVIG™ not being completely removed by the washing steps. At the time that the serum/IgG-virus mixtures are added to the target cells, each serum, IVIG™ or HIVIG™ also is added to target cells without preincubation with virus. These wells are treated in parallel with the experimental cultures. After 7 days of culture, the supernatant from each well is mixed 1:1 with that of the negative control and the p24 antigen concentration is quantitated. A measurement that is less that 50% the value of the negative control is considered non-specific inhibition of p24 antigen, which can be due to the presence of residual p24 antibodies.

Although the invention has been described with reference to the examples above, it should be understood that various modifications can be made without departing from the spirit of the invention. Accordingly, the invention is limited only by the following claims. All references cited above are incorporated herein in their entirety.

What is claimed is:

1. A polynucleotide comprising a chimeric CHIV retroviral genome comprising a polynucleotide sequence encoding an intact HIV-1 envelope protein, one or more segments of the caprine arthritis encephalitis virus (CAEV) viral genome sufficient to render nonpathogenic to a primate a resulting retroviral particle produced by expressing the chimeric retroviral genome in a mammalian host cell, wherein the chimeric genome comprises expression control segments including the 5' and 3' LTR regions obtained from CAEV sufficient to direct expression of the chimeric retroviral genome in a mammalian host cell, and wherein the retroviral particle produced by expressing the retroviral genome in a host cell generates an immune response against HIV-1.

2. The polynucleotide of claim 1, wherein the segments of the CAEV viral genome are obtained from CAEV-Co.

3. The polynucleotide of claim 1, wherein the polynucleotide sequence encoding the HIV-1 envelope protein is obtained from the $SF_{33}$ strain of HIV-1.

4. The polynucleotide of claim 1, wherein the polynucleotide sequence encoding the HIV-1 envelope protein is from the $SF_{162}$ strain of HIV-1.

5. A purified CHIV retrovirus comprising the polynucleotide of claim 1.

6. The purified retrovirus of claim 5, wherein the retrovirus is cytopathic in vitro.

* * * * *

UNITED STATES PATENT AND TRADEMARK OFFICE
CERTIFICATE OF CORRECTION

PATENT NO. : 6,602,505 B2
DATED : August 5, 2003
INVENTOR(S) : Angeline Douvas et al.

It is certified that error appears in the above-identified patent and that said Letters Patent is hereby corrected as shown below:

<u>Title page,</u>
Item [57], ABSTRACT,
Line 1, insert -- present -- after "The".

<u>Column 19,</u>
Line 31, "the" should read -- a --.

Signed and Sealed this

First Day of June, 2004

JON W. DUDAS
*Acting Director of the United States Patent and Trademark Office*

SEQUENCE LISTING

```
<160> NUMBER OF SEQ ID NOS: 3

<210> SEQ ID NO 1
<211> LENGTH: 124
<212> TYPE: DNA
<213> ORGANISM: Artificial Sequence
<220> FEATURE:
<223> OTHER INFORMATION: 5' CAEV-Co-HIV p162/3'SX Junction
<221> NAME/KEY: CDS
<222> LOCATION: (18)...(83)

<400> SEQUENCE: 1
ggaatatctc ttagagg atg agt gaa gaa ctg cct caa aga agg gag aca        50
                   Met Ser Glu Glu Leu Pro Gln Arg Arg Glu Thr
                    1               5                   10 cat cca gaa gaa ctt gta agg aac gta cgg tga atcgatgcat gcacagagga    103
His Pro Glu Glu Leu Val Arg Asn Val Arg  *
            15                  20 gagcaaggaa tggagccagt a                                              124

<210> SEQ ID NO 2
<211> LENGTH: 66
<212> TYPE: DNA
<213> ORGANISM: Artificial Sequence
<220> FEATURE:
<223> OTHER INFORMATION: DNA sequence encoding for the first 21 amino
      acids of normal CAEV tat sequence then truncated by engineered
      stop
```

-continued

```
<221> NAME/KEY: CDS
<222> LOCATION: (1)...(66)

<400> SEQUENCE: 2
atg agt gaa gaa ctg cct caa aga agg gag aca cat cca gaa gaa ctt       48
Met Ser Glu Glu Leu Pro Gln Arg Arg Glu Thr His Pro Glu Glu Leu
 1               5                  10                  15
gta agg aac gta cgg tga                                               66
Val Arg Asn Val Arg  *
             20

<210> SEQ ID NO 3
<211> LENGTH: 88
<212> TYPE: DNA
<213> ORGANISM: Artificial Sequence
<220> FEATURE:
<223> OTHER INFORMATION: 3' CAEV-Co-HIV p162/3'SX Junction
<400> SEQUENCE: 3
ctagaagaat aagacagggc tttgaaaggg ctttgctata agctcgaggc ggccgccgta     60
cgaatcttgg aagctcgagt ggctcgag                                        88
```